United States Patent [19]

Immel et al.

[11] Patent Number: 5,371,294

[45] Date of Patent: * Dec. 6, 1994

[54] PROCESS FOR THE PREPARATION OF A MIXTURE OF CYCLOHEXYLAMINE AND DICYCLOHEXYLAMINE

[75] Inventors: Otto Immel; Hans-Josef Buysch; Gerhard Darsow, all of Krefeld, Germany

[73] Assignee: Bayer Aktiengesellschaft, Leverkusen, Germany

[*] Notice: The portion of the term of this patent subsequent to Jun. 21, 2011 has been disclaimed.

[21] Appl. No.: 955,957

[22] Filed: Oct. 2, 1992

[30] Foreign Application Priority Data

Oct. 11, 1991 [DE] Germany ............... 4133675

[51] Int. Cl.$^5$ ............... C07C 209/16; C07C 209/18
[52] U.S. Cl. ............... 564/450; 564/402; 564/403; 564/431; 564/447; 564/457; 564/462
[58] Field of Search ............... 564/450, 451, 402, 403, 564/431, 457, 462, 447

[56] References Cited

U.S. PATENT DOCUMENTS

| | | | |
|---|---|---|---|
| 2,571,016 | 10/1951 | Dankert et al. | 564/447 |
| 3,351,661 | 11/1967 | Van Munster | 260/563 |
| 3,364,261 | 1/1968 | Van Munster | 260/563 |
| 3,799,867 | 3/1974 | Cardwell et al. | 208/139 |
| 4,429,155 | 1/1984 | Goetz et al. | 564/402 |
| 4,487,966 | 12/1984 | Fiedler et al. | 564/454 |
| 4,503,251 | 3/1985 | Gray et al. | 564/450 |
| 4,666,881 | 5/1987 | Wood et al. | 502/325 |
| 4,952,549 | 8/1990 | Immel et al. | 564/450 |

FOREIGN PATENT DOCUMENTS

| | | |
|---|---|---|
| 0053696 | 10/1981 | European Pat. Off. . |
| 0053817 | 12/1981 | European Pat. Off. . |
| 053819 | 6/1982 | European Pat. Off. ............ 564/402 |
| 227868 | 7/1987 | European Pat. Off. . |
| 0324984 | 7/1989 | European Pat. Off. . |
| 1530477 | 6/1968 | France . |
| 2115860 | 7/1972 | France . |
| 1276032 | 4/1965 | Germany . |
| 1031169 | 3/1965 | United Kingdom . |

*Primary Examiner*—Glennon H. Hollrah
*Assistant Examiner*—Scott C. Rand
*Attorney, Agent, or Firm*—Sprung Horn Kramer & Woods

[57] ABSTRACT

Cyclohexylamine and dicyclohexylamine can be prepared as a mixture with one another by reaction of phenol with aniline, ammonia or a mixture of aniline and ammonia in the presence of hydrogen over a catalyst, the reaction being carried out according to the invention over a palladium catalyst which has a support of niobic acid or tantalic acid or a mixture of niobic acid and tantalic acid or a support containing such acids. The reaction is carried out at 100°–220° C. under an $H_2$ partial pressure of 0.5–500 bar.

15 Claims, No Drawings

PROCESS FOR THE PREPARATION OF A MIXTURE OF CYCLOHEXYLAMINE AND DICYCLOHEXYLAMINE

BACKGROUND OF THE INVENTION

1. Field of the Invention

The present invention relates to a process for the preparation of cyclohexylamine and dicyclohexylamine as a mixture with one another by reaction of phenol with aniline and/or ammonia under hydrogenating conditions in the presence of a palladium catalyst. The catalyst has a support of niobic acid, tantalic acid or a mixture of niobic acid and tantalic acid or a support containing such acids.

2. Description of the Related Art

An important method for the preparation of optionally substituted cyclohexylamine or dicyclohexylamine is the reduction of the corresponding aromatic nitro compounds (Houben-Weyl, Methoden der Org. Chemie (Methods of Organic Chemistry), Volume XI/1, page 360 et seq.) to primary aromatic amines and hydrogenation of the nucleus thereof. However, the nitration often proceeds non-uniformly and therefore almost always gives isomer mixtures.

There is also the possibility of converting phenols into cyclohexanones by partial hydrogenation, and of reacting these with ammonia and hydrogen to give cyclohexylamines (German Auslegeschriften 1,124,487, German Auslegeschriften 1,298,098, German Ausleges-chriften 1,144,267, U.S. Pat. No. 3,124,614, CH 463,493, German Offenlegungsschrift 2,045,882 and Houben-Weyl, loc. cit., pages 611–617).

The preparation routes mentioned require several process steps which are independent of one another, and they are therefore quite cumbersome and not particularly economical.

According to previous knowledge, one-stage direct conversion of unsubstituted phenol into cyclohexylamine using ammonia and hydrogen is achieved in the presence of ruthenium catalysts or rhodium catalysts (JP-A 40/34,677, FR 1,427,543, GB 1,031,169 and German Auslegeschrift 1,276,032). The following catalysts have been employed for the abovementioned hydrogenation of the nucleus of aniline to give cyclohexylamine: cobalt catalysts with a basic addition (GB 969,542), Raney cobalt (JP 68/03180), ruthenium catalysts (German Auslegeschrift 1,106,319), ruthenium catalysts doped with alkali metal compounds U.S. Pat. No. 3,636,108) or nickel catalysts (German Patent Specification 805,518).

Most of the processes mentioned are operated under pressure and give chiefly cyclohexylamine, alongside only a little dicyclohexylamine. The dicyclohexylamine is therefore often prepared by other processes, for example by pressure hydrogenation of diphenylamine using a ruthenium catalyst (German Auslegeschrift 1,106,319). Dicyclohexylamine is furthermore formed in the reaction of cyclohexanone with cyclohexylamine in the presence of a palladium/charcoal catalyst under a hydrogen pressure of about 4 bar (FR 1,333,692). The process of the above German Patent Specification 805,518 is chiefly directed towards the production of dicyclohexylamine, but operates with cumbersome recyclings of by-product. Dicyclohexylamine furthermore is formed in the catalytic reaction of phenol with hydrogen and ammonia (U.S. Pat. No. 3,351,661) and in the hydrogenation of a mixture of aniline and phenol (U.S. Pat. No. 2,571,016). In contrast, monocyclohexylamine is formed from phenol, ammonia and hydrogen in the presence of a noble metal applied to a support (EP 53,817); this catalyst preferably contains a basic substance and/or an element from group Ib or IIb of the periodic table of the elements (Mendeleev). Aniline is obtained from phenol and ammonia in the presence of hydrogen using a palladium/cobalt catalyst on an aluminium spinel (EP 53,696).

The catalysts of the processes mentioned have an unsatisfactory service life; moreover, sometimes considerable amounts of cyclohexane are formed as a useless waste product. There was therefore the desire to develop a process which can be used on an industrial scale, in which the loss due to the formation of cyclohexane is suppressed and the service life of the catalyst used is improved. There was furthermore the desire for a process in which both cyclohexylamine and dicyclohexylamine are formed, the amount of which can be adjusted variably according to the demand for these substances.

SUMMARY OF THE INVENTION

It has been found, surprisingly, that the requirements mentioned can be achieved if a palladium catalyst, the support of which is niobic acid, tantalic acid or a mixture of the two, is employed or which contains such acids.

The invention therefore relates to a process for the preparation of a mixture of cyclohexylamine and dicyclohexylamine by reaction of phenol with aniline, ammonia or a mixture of aniline and ammonia in the presence of hydrogen over a catalyst, which is characterised in that a palladium catalyst which has a niobic acid or tantalic acid or niobic acid/tantalic acid support or a support containing such acids and contains 0.05–5% by weight of palladium, based on the total weight of the catalyst, is employed and the reaction is carried out at 100°–220° C. under an $H_2$ partial pressure of 0.5–500 bar.

DETAILED DESCRIPTION OF THE INVENTION

The palladium content of the catalyst to be employed according to the invention is preferably 0.1–4% by weight, particularly preferably 0.1–3% by weight, based on the total weight of the catalyst.

The catalysts according to the invention accordingly are distinguished above all by the combination of palladium with niobic acid acid and/or tantalic acid as the support or on the support. Compared with the known support catalysts, such catalysts produce higher yields of dicyclohexylamine and are distinguished by an excellent service life.

As is known, niobic acid is a niobium pentoxide hydrate ($Nb_2O_5.nH_2O$), which can be obtained, for example, by treatment of aqueous solutions of niobic acid salts with strong mineral acids or by treatment of niobium alcoholates, niobic acid halides or niobic acid esters with water, acids or bases. Niobic acid precipitated in this way is dried and is then a sparingly soluble solid compound, the residual water content of which is not defined, although a niobic acid prepared in this way appears externally to be a dry powder. The preparation of niobic acid (niobium pentoxide hydrate) is described, for example, in Gmelins Handbuch der anorg. Chemie (Gmelins Handbook of inorganic Chemistry), 8th Edition, Niobium part B1, page 49.

Tantalic acid or tantalum pentoxide hydrate (Ta$_2$O$_5$·nH$_2$O) for the preparation of the catalysts to be employed according to the invention can be prepared in an analogous manner by hydrolysis of tantalum(V) salts, tantalum(V) alcoholates or other suitable hydrolysable tantalum(V) compounds. The hydrolysis takes place in an analogous manner to that described above for niobic acid; it is described, for example, in Gmelins Handbuch der anorg. Chemie (Gmelins Handbook of Inorganic Chemistry), 8th Edition, Tantalum part B1, page 53 (1970) and in Chem. Lett. 1988 page 1573. That which is described for one of the two elements also applies in principle to the other. The large chemical similarity of the two elements and their compounds also manifests itself in the fact that they are largely associated with one another in their natural deposits.

Niobic acid, especially that which contains a tantalic acid content of 0.0001–10 mol %, based on the total number of moles of niobic and tantalic acid, originating from the natural source, is preferably employed as the support.

So that the niobic and/or tantalic acid can be brought into the pieced form favourable for use as a fixed bed catalyst, for example, the moist precipitate of the hydrolysis is kneaded thoroughly in a kneader and processed to shaped pieces in a granulating apparatus. The moist shaped articles are then dried, for example at 120° C., and calcined at 200°–400° C. for 0.5–5 hours. This results in a BET surface area of 5–350 m$^2$/g. To produce granules, extrudates or beads, niobic and/or tantalic acid can also be pressed and granulated with a binder.

Niobic or tantalic acid is an active substance, in respect of the catalyst according to the invention, the activity of which is also retained by mixing with other solids. Examples of suitable solids are aluminium oxide, titanium dioxide, zinc oxide, magnesium oxide, iron oxide, silicon dioxide, graphite and others. These solids can also be employed as binders in the manner described above. Mixtures of niobic or tantalic acid with these solids can be employed in a ratio of 5:95–99:1, preferably 50:50–98:2. Preferred catalysts which can be employed according to the invention contain niobic or tantalic acid or a mixture of both without a further addition. In the case of combination with one of the abovementioned solids, a particularly effective catalyst support is obtained if Al$_2$O$_3$ granules are impregnated with a solution of a niobium and/or tantalum compound such that the content of niobic and/or tantalic acid of the support prepared in this way is 0.2–30, preferably 0.5–10% by weight.

The catalyst can be prepared by impregnating palladium, in the form of a soluble compound, onto niobic acid, tantalic acid or a mixture of the two or onto one of the abovementioned other supports containing niobic and/or tantalic acid, drying the support after the impregnation, and employing the catalyst in the form which then exists or after pretreatment with hydrogen at 120°–400° C., preferably at 150°–340° C. This H$_2$ pretreatment is preferably carried out in the reactor in which the process according to the invention is subsequently carried out.

for this purpose, the catalyst support is in the form of pellets, beads or fragments having dimensions of about 1–10 mm. The palladium compound is impregnated on in a manner which is known in principle to the expert. The drying is carried out, for example, at 100°–140° C. under reduced to normal pressure, for example under 1–1000 mbar.

The palladium compounds employed can be dissolved in water or in suitable organic solvents. They are preferably dissolved in organic solvents, such as simple alcohols, ketones, nitriles or cyclic ethers. Examples of such solvents are methanol, ethanol, acetone, acetonitrile and dioxane. Suitable palladium compounds are, for example, the chloride, nitrate or acetate.

According to the invention, the catalysts described can be employed in an outstanding manner for the hydrogenating reaction of optionally substituted aniline with phenol and for the hydrogenating reaction of a phenol/ammonia mixture or a three-component mixture of phenol/aniline/ammonia. A mixture of cyclohexylamine and dicyclohexylamine of the formulae

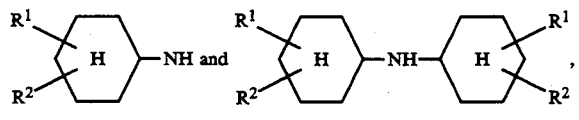

(I)          (II)

in which

R$^1$ and R$^2$ independently of one another denote hydrogen, C$_1$–C$_4$-alkyl or C$_1$–C$_4$-alkoxy, is formed in this reaction.

The cyclohexylamine and dicyclohexylamine accordingly have the substitution pattern of the phenol or aniline on which they are based, of the formula

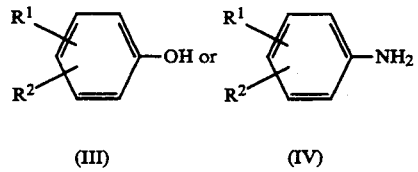

(III)          (IV)

in which

R$^1$ and R$^2$ have the meaning given.

In a particularly surprising manner, the amount of dicyclohexylamine formed in relation to the amount of monocyclohexylamine can be changed as a function of the hydrogenation temperature using the catalysts described, controlled preparation of relatively large amounts of dicyclohexylamine being possible. If the reaction is carried out in the upper part of the temperature range according to the invention, the content of monocyclohexylamine increases in relation to that of the dicyclohexylamine, and vice versa.

The alkyl and alkoxy substituents mentioned are, for example: methyl, ethyl, propyl, isopropyl, butyl, isobutyl, methoxy, ethoxy, propoxy, isopropoxy, butoxy or isobutoxy. The substituents mentioned preferably have 1–2 C atoms, and particularly preferably are methyl or methoxy. Furthermore, preferably, R$^2$ denotes hydrogen, while R$^1$ has the scope of meanings mentioned. The process according to the invention is particularly preferably directed towards hydrogenation of the nucleus of unsubstituted aniline in the presence of unsubstituted phenol and to the hydrogenation reaction of a phenol/ammonia mixture.

The process according to the invention can be carried out in a relatively wide pressure range, which is characterised by an H$_2$ partial vapour pressure of 0.5–500 bar, preferably 2–400 bar, particularly preferably 100–400 bar, especially preferably 150–350 bar. The reaction can be carried out here, for example, in the trickle phase over a fixed bed catalyst or in an autoclave. This opens up the possibility both of a discontinuous and of a continuous procedure. For industrial purposes, the reaction is preferably carried out continuously, advantageously in the trickle phase. An amount of 0.05–2 kg, preferably 0.1–1 kg, particularly preferably 0.15–0.6 kg of starting material per liter of catalyst and hour is set as the catalyst loading.

In the reaction of phenol with aniline, a molar ratio of the two substances of 10:1–1:10 is chosen; the preferred molar ratio is 3:1–1:3. In the reaction of phenol and ammonia, a molar ratio of phenol:ammonia=1:20–1:1, preferably 1:10–1:2, is chosen.

The reaction mixture formed in the process according to the invention can be separated into cyclohexylamine and dicyclohexylamine in the customary manner, for example by distillation. Starting substances which have not reacted completely, such as phenol or aniline, or incompletely hydrogenated reaction products, such as N-cyclohexylaniline, can be recycled in a manner known to the expert.

The cyclohexylamines and dicyclohexylamines having the scope of meanings mentioned are used for the preparation of antiageing agents for rubbers and plastics, as corrosion inhibitors and as a precursor for plant protection agents and textile auxiliaries.

EXAMPLE 1

75 g of niobic acid, $Nb_2O_5 \cdot nH_2O$, which had been shaped to 5 mm tablets with addition of 3.5% of graphite powder, were impregnated with a solution which had been prepared from 1.56 g of Pd acetate and 26.8 g of acetonitrile. The niobic acid tablets impregnated in this manner were dried under a waterpump vacuum at 100° C. for 18 hours. The niobic acid was then impregnated again with 1% of Pd in the same manner. 60 ml (61 g) of the catalyst thus prepared were introduced into a vertically arranged pressure tube (diameter 14 mm, length 70 cm) which was heated using an oil thermostat. The inter-grain volume was filled with fine sea sand (0.2–0.4 mm). The catalyst was first activated with hydrogen at 250° C. under 270 bar for 3 hours, 40 liters of hydrogen being released per hour at the lower end of the reaction tube. The hydrogenation of aniline as a mixture with phenol was then started at 182° C. under 270 bar, the aniline/phenol mixture and hydrogen being passed onto the catalyst from the top. The liquid trickled downwards over the catalyst into a separator. 26–62 liters of hydrogen were released at the top of the separator. The amount of aniline/phenol fed in continuously corresponded to a catalyst loading in the range of 0.2–0.3 g/ml of catalyst/h.

TABLE 1

(relating to Example 1): Hydrogenating reaction of phenol and aniline

| Loading (g/ml·h) | Temperature (°C.) | Product (% by weight) | | | | | |
|---|---|---|---|---|---|---|---|
| | | Anol | Phenol | Aniline | CA | NCHA | DCA |
| 0.23[1] | 160 | 2.3 | 13.3 | 18,2 | 2.0 | 8.2 | 54.5 |
| 0.24[1] | 171 | — | 2.7 | 4,8 | 0.8 | 6.7 | 81.9 |
| 0.28[1] | 196 | 0.7 | — | 0.1 | 6.7 | 0.3 | 92.0 |
| 0.28[2] | 206 | 5.8 | — | — | 2.1 | 0.1 | 91.6 |
| 0.22[2] | 208 | 4.4 | — | — | 2.6 | 0.1 | 92.1 |
| 0.19[2] | 231 | 7.4 | — | 0.1 | 17.3 | 0.1 | 74.0 |

[1] Aniline:phenol = 2:1 molar;
[2] Aniline:phenol = 1:1 molar; Anol = cyclohexanol; CA = cyclohexylamine; NCHA = N-cyclohexylaniline; DCA = dicyclohexylamine

EXAMPLE 2

400 g of spherical $\gamma$-$Al_2O_3$ having a diameter of 2–5 mm and a specific surface area of 350 m²/g were impregnated with a solution of 23.3 g of $NbCl_5$ in 120 g of 37% strength hydrochloric acid, and then dried at 120° C. The catalyst support was then impregnated with 410 g of a 16.9% strength by weight aqueous ammonia solution, and subsequently washed free from chloride with water and dried again. 150 g of the catalyst support thus prepared were impregnated with a solution which had been prepared from 3.13 g of Pd acetate and 40 g of acetonitrile. After renewed drying at 120° C., the catalyst was ready for use. The reaction of phenol with $NH_3$ and hydrogen was carried out in a pressure tube of the type employed in Example 1 using 60 ml (53 g) of the catalyst thus prepared. The catalyst was first activated in a stream of hydrogen at 250° C. under 270 bar for 3 hours. 12–27 g of phenol and 4.6–5.8 g of liquid ammonia per hour were introduced onto the activated catalyst from the top, while the pressure in the hydrogenating apparatus was kept at 280 bar with a constant stream of hydrogen also passed from the top downwards. The liquid trickled downwards over the catalyst into a pressure separator. Hydrogen, which contained excess ammonia, was released (110–170 liters/hour) at the top of the separator, in order to maintain a continuous stream of gas in the reaction tube. The apparatus was operated continuously, the reaction temperature being varied between 135° and 215° C.

TABLE 2

(relating to Example 2): Hydrogenating reaction of phenol with ammonia

| Phenol (g/h) | NH₃ (g/h) | Temperature (°C.) | Product (% by weight) | | | | | |
|---|---|---|---|---|---|---|---|---|
| | | | Anol | Phenol | Aniline | CA | NCHA | DCA |
| 15.4 | 5.8 | 135 | 8.7 | 0.5 | 0.5 | 22.5 | 0.2 | 67.8 |
| 12.1 | 5.5 | 145 | 1.0 | 0.3 | 0.1 | 30.1 | 0.1 | 68.3 |
| 27.5 | 5.0 | 200 | 5.1 | — | — | 21.9 | — | 73.0 |
| 22.2 | 5.5 | 215 | 5.9 | — | — | 22.7 | — | 71.4 |

Anol, CA, NCHA and DCA as in Table 1.

What is claimed is:

1. A continuous process for the preparation of a mixture of cyclohexylamine and dicyclohexylamine by reaction of phenol with aniline, or a mixture of aniline and ammonia in the presence of hydrogen over a catalyst, wherein a palladium catalyst which has a niobic acid or tantalic acid or niobic acid/tantalic acid support or a support containing such acids and contains 0.05–5% by weight of palladium, based on the total weight of the catalyst, is employed and the reaction is carried out at 100°–220° C. under an $H_2$ partial pressure of 0.05–500 bar and wherein the amount of cyclohexylamine relative to the amount of dicyclohexylamine can be varied by varying the temperature at which said reaction is carried out within said temperate range.

2. The process of claim 1, wherein the reaction is carried out under an $H_2$ partial pressure of 2–400 bar.

3. The process of claim 2, wherein the reaction is carried out under an $H_2$ partial pressure of 100–400 bar.

4. The process of claim 3, wherein the reaction is carried out under an $H_2$ partial pressure of 150–350 bar.

5. The process of claim 1, wherein the molar ratio of phenol to aniline is 10:1–1:10.

6. The process of claim 5, wherein a molar ratio of phenol:aniline=3:1–1:3 is chosen.

7. The process of claim 1, wherein phenol and ammonia are reacted and a molar ratio of 1:20–1:1 is chosen.

8. The process of claim 7, wherein a molar ratio of phenol:$NH_3$=1:10–1:2 is chosen.

9. The process of claim 1, wherein the catalyst contains 0.1–4% by weight of palladium, based on the total weight of the catalyst.

10. The process of claim 9, wherein the catalyst contains 0.1–3% by weight of palladium, based on the total weight of the catalyst.

11. The process of claim 1, wherein the reaction is carried out under a catalyst loading of 0.05–2 kg of starting product per liter of catalyst per hour.

12. The process of claim 11, wherein the reaction is carried out under a catalyst loading of 0.1–1 kg of starting product per liter of catalyst per hour.

13. The process of claim 12, wherein the reaction is carried out under a catalyst loading of 0.15–0.6 kg of starting product per liter of catalyst per hour.

14. The process of claim 1, wherein the catalyst support is an $Al_2O_3$ with a content of 0.2–30% by weight of niobic and/or tantalic acid.

15. The process of claim 14, wherein the $Al_2O_3$ has a content of 0.2–10% by weight of niobic and/or tantalic acid.

* * * * *

UNITED STATES PATENT AND TRADEMARK OFFICE
CERTIFICATE OF CORRECTION

PATENT NO. : 5,371,294
DATED : December 6, 1994
INVENTOR(S) : Otto Immel, et al.

It is certified that error appears in the above-identified patent and that said Letters Patent is hereby corrected as shown below:

Col. 6, Line 67                  Delete "0.05-500 "and substitute -- 0.5-500 --

Signed and Sealed this

Twenty-first Day of September, 1999

Attest:

Q. TODD DICKINSON

*Attesting Officer*          *Acting Commissioner of Patents and Trademarks*